(12) United States Patent
Zadgaonkar et al.

(10) Patent No.: US 10,643,639 B2
(45) Date of Patent: *May 5, 2020

(54) SYSTEM AND METHOD FOR DETERMINING CARDIAC PARAMETERS AND PHYSIOLOGICAL CONDITIONS BY ANALYSING SPEECH SAMPLES

(71) Applicants: Ajit Arun Zadgaonkar, Riverside, CA (US); Arun Shrihari Zadgaonkar, Riverside, CA (US)

(72) Inventors: Ajit Arun Zadgaonkar, Riverside, CA (US); Arun Shrihari Zadgaonkar, Riverside, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 16/002,003

(22) Filed: Jun. 7, 2018

(65) Prior Publication Data
US 2018/0374499 A1 Dec. 27, 2018

(30) Foreign Application Priority Data
Jun. 21, 2017 (IN) .............................. 201721021745

(51) Int. Cl.
*A61B 5/00* (2006.01)
*A61B 5/02* (2006.01)
(Continued)

(52) U.S. Cl.
CPC ............ *G10L 25/66* (2013.01); *A61B 5/4803* (2013.01); *G10L 15/02* (2013.01); *G10L 15/22* (2013.01);
(Continued)

(58) Field of Classification Search
CPC ......... G10L 25/66; G10L 15/02; G10L 15/22; G10L 2015/025; A61B 5/002;
(Continued)

(56) References Cited

U.S. PATENT DOCUMENTS

2012/0220899 A1* 8/2012 Oh ....................... A61B 5/4082
600/586
2012/0265024 A1* 10/2012 Shrivastav ............... A61B 5/40
600/300

(Continued)

OTHER PUBLICATIONS

Mesleh et al., "Heart Rate Extraction from Vowel Speech Signals", 2012, Journal of Computer Science and Technology, all pages (Year: 2012).*

(Continued)

*Primary Examiner* — Sonia L Gay (57) ABSTRACT

The present disclosure describes a system and method for determining cardiac parameters and physiological conditions of a user by analysing speech samples of said user. A user device of the user may record specifics of speech and use these specifics of speech as a speech sample of user's utterance. The user device may transmit the speech samples to a backend system. The system may isolate phonation segments from the speech samples. The system may filter one or more phonation segments. The system may isolate uttered speech segments from one or more phonation segments. The system may perform an acoustic-phonetic analysis of the uttered speech segments. The acoustic-phonetic analysis may use plurality of features for the analysis. The IPA phonemes may be used to derive speech markers that correspond to specific cardiac parameters and physiological conditions. The system may generate a resulting report after analysis which is transmitted to the user.

17 Claims, 3 Drawing Sheets

(51) Int. Cl.
  *A61B 5/021* (2006.01)
  *A61B 5/024* (2006.01)
  *A61B 5/0452* (2006.01)
  *A61B 5/107* (2006.01)
  *A61B 5/145* (2006.01)
  *G10L 25/66* (2013.01)
  *G10L 15/02* (2006.01)
  *G10L 15/22* (2006.01)
  *G16H 50/20* (2018.01)

(52) U.S. Cl.
  CPC ............ *G16H 50/20* (2018.01); *A61B 5/0002* (2013.01); *A61B 5/021* (2013.01); *A61B 5/024* (2013.01); *A61B 5/02007* (2013.01); *A61B 5/02028* (2013.01); *A61B 5/0452* (2013.01); *A61B 5/1073* (2013.01); *A61B 5/1075* (2013.01); *A61B 5/14546* (2013.01); *G10L 2015/025* (2013.01)

(58) Field of Classification Search
  CPC .............. A61B 5/02007; A61B 5/4803; A61B 5/02028; A61B 5/021; A61B 5/024; A61B 5/0452; A61B 5/1073; A61B 5/1075; G16H 50/20
  See application file for complete search history.

(56) References Cited

U.S. PATENT DOCUMENTS

2016/0089047 A1* 3/2016 Jonnada ............ A61B 5/04012
                                                          600/516
2019/0362740 A1* 11/2019 Hauptman ............... A61B 5/02

OTHER PUBLICATIONS

Kaur et al., "Extraction of Heart Rate Parameters Using Speech Analysis", 2014, International Journal of Science and Research, all (Year: 2014).*

* cited by examiner

SYSTEM AND METHOD FOR DETERMINING CARDIAC PARAMETERS AND PHYSIOLOGICAL CONDITIONS BY ANALYSING SPEECH SAMPLES

CROSS-REFERENCE TO RELATED APPLICATIONS AND PRIORITY

The present application claims priority from Indian provisional patent application no. 201721021745 filed on the 21 Jun. 2017, the details of which are incorporated herein by a reference.

TECHNICAL FIELD

The present subject matter described herein, in general, relates to a system and method for determining cardiac parameters and physiological conditions of a user by analysing speech samples of the user.

BACKGROUND

There are several cardiological parameters which impact health throughout human life. These parameters play a key role in the well-being of people of all ages. An abnormality in an or it's functionality in cardiovascular system may result into weakened heart and can lead to heart failure or backup of blood into the lungs. Neglect of undesirable cardiovascular conditions (e.g. high blood pressure, high pulse pressure, arrhythmia, stroke, heart and valve issues, and coronary artery thickening) could lead to permanent health damage or even loss of life. Cardiac arrhythmia is a condition related to heart beats. Heart beats above 100 beats/min is too fast and is termed as tachycardia and heart rate slow below 60 beats/min is called bradycardia. They are important from heart failure or cardiac arrest point of view.

The methods that exist today to analyze cardiovascular health are pathological labs and medical imaging which require human bodily fluids and human body contact. Existing methods to determine cardiological, cardiovascular health and dimensions of heart rely on specific devices such as ECG device, echocardiogram device etc. and on obtaining blood samples for measurement of cholesterol from the patient/user and performing pathological laboratory tests. For example, following tests are conducted using medical devices:

ECG/EKG tests and measurements are conducted by ECG devices and are operated by trained medical professionals.

Echocardiogram is conducted to get the dimensions of heart, ESV, EDV, SV, Ef values. This requires sophisticated echo devices, facility and trained medical professionals to operate it.

Heart rate is measured by several devices that needs direct physical access to human body to measure the pulse rate.

Blood pressure is measured with devices that specialize in measuring blood pressure. These devices connect to the human body to measure blood pressure.

Dimensions of the aorta is usually measured with medical imaging techniques.

Most cardiovascular tests are currently conducted by laboratory analysis of blood samples, physical examinations or by performing an electrocardiogram (ECG/EKG) or echocardiogram (echo) tests. These tests can be intrusive in nature, e.g. Transesophageal echocardiography (TEE), often require tests be administered by medically trained professionals and usually require patients to travel to clinics or hospitals or laboratory offices. These invasive tests are uncomfortable for many, are usually expensive, and impose a logistical burden on patients who might not be able to travel, and often require fasting prior to the tests.

Typically, the only time most patients go and see a doctor or undergo tests is if they have severe symptoms. Doing early testing helps with early diagnosis, which significantly assists in reducing health risks and being able to successfully treat a patient for a medical problem. Many patients do not seek the appropriate medical treatment even when they observe debilitating symptoms due to the inconvenience or obstacles they face to conduct such testing or visiting a doctor.

There is no existing non-invasive (i.e., not requiring a body fluid sample) methods to determine results that are otherwise accessible only to ECG, echocardiogram, heart rate and blood pressure monitoring device. Hence, it is a long-lasting need to eliminate the burden of conducting onerous laboratory tests to easily obtain cardiological system related information.

SUMMARY

This summary is provided to introduce the concepts related to a system and method for determining cardiovascular health, associated properties and dimensions of user's organ(s) and the concepts are further described in the detailed description. This summary is not intended to identify essential features of the claimed subject matter nor it is intended to use in determining or limiting the scope of claimed subject matter.

In one embodiment, a system for determining cardiovascular health, associated properties and dimensions of user's organs) by analysing speech samples of the said user is disclosed. The system may include a processor and a memory coupled with the processor. The processor may be configured to execute a plurality of programmed instructions stored in the memory. The processor may execute a programmed instruction for guiding a user to utter specifics of a speech via a user device communicatively coupled with the processor. Further, the processor may execute a programmed instruction for recording one or more speech samples associated with the user based upon the specifics of speech uttered by the user. The processor may further execute a programmed instruction for isolating one or more phonation segments from the one or more speech samples. Further, the processor may execute a programmed instruction for filtering one or more phonation segments to remove noise from the one or more phonation segments. The processor may further execute a programmed instruction for isolating one or more uttered speech segments from the one or more phonation segments filtered. Further, the processor may execute a programmed instruction for performing acoustic-phonetic analysis of the one or more uttered speech segments to extract one or more speech features in order to determine speech markers and the corresponding cardiovascular health, associated properties and dimensions of organs of the user. Furthermore, the processor may execute a programmed instruction for determining one or more speech markers that corresponds to cardiovascular health, associated properties and dimensions of organs of the user.

In accordance with aspects of the present disclosure, the processor may generate report based on cardiovascular health, associated properties and dimensions of organs of the user in order to determine cardiovascular health, associated properties and dimensions of user's organ(s), wherein the report generated may further be transmitted to the user device.

In accordance with aspects of the present disclosure, the specifics of speech may comprise attributes selected from a group comprising of a frequency and formants. Further, the specifics of speech may include, but not limited to, one or more of words, letters, phonations, and the like.

In accordance with aspects of the present disclosure, the one or more speech features may include, but not limited to, utterance of the user, vowel and consonants under isolated and/or vowel consonant (VC), consonant Vowel (CV) environment, formants of the utterance, pitch of the utterance, vocal intensity of the utterance, speech quality of the utterance, vowel onset point (VOP), energy transition, values of dispersion and bandwidth, voice onset time (VOT), articulatory rate, shimmer, jitter, spectrogram, and the like.

In accordance with aspects of the present disclosure, the speech markers corresponding to determine cardiovascular health, associated properties and dimensions of user's organ(s) by analysing speech samples may include, but not limited to ECG wave heart rate speech marker, P-wave duration speech marker, PR-interval speech marker, PR-segment speech marker, QRS-duration speech marker, ST-segment speech marker, ST-interval speech marker, T-duration speech marker, QT interval speech marker, QTc interval speech marker, volume and dimensions of heart, difference of myocardial thickness between left and right myocardial thickness, End Systolic Volume (ESV) speech marker, End Diastolic Volume (EDV), Stroke Volume (SV) speech marker, Ejection Fraction (Ef) speech marker, heart rate speech marker, pulse pressure speech marker, diastolic blood pressure speech marker, systolic blood pressure speech marker, dimensions of aorta speech marker and cholesterol speech markers.

In another embodiment, a method for determining cardiovascular health, associated properties and dimensions of user's organ(s) by analysing speech samples of the said user is disclosed. The method may include interactively guiding, via a user device communicatively coupled with a processor, a user to utter specifics of a speech. Further, the method may include recording, via the user device, one or more speech samples associated with the user based upon the specifics of speech uttered by the user. The method may further include isolating, via the processor, one or more phonation segments from the one or more speech samples. Further, the method may include filtering, via the processor, one or more phonation segments to remove noise from the one or more phonation segments. Further, the method may include isolating, via the processor, one or more uttered speech segments from the one or more phonation segments filtered in order to remove noise from the one or more phonation segments. The method may further include performing, via the processor, acoustic-phonetic analysis of the one or more uttered speech segments to extract one or more speech features. Further, the method may include performing, via the processor, an acoustic-phonetic analysis of the uttered speech segments in order to determine speech markers and the corresponding cardiovascular health, associated properties and dimensions of organ(s) of the user. The acoustic-phonetic analysis may use a plurality of features associated with the user for analysis. Furthermore, the method may include determining, via the processor, one or more speech markers and the corresponding cardiovascular health, associated properties and dimensions of organ(s) of the user based upon the one or more speech features.

In accordance with aspects of the present disclosure, the International Phonetic alphabets (IPA) phonemes may be used to derive speech markers that corresponds to cardiovascular health, associated properties and dimensions of organs of the user, wherein the IPA may include, but are not limited to, velar consonants, palatal consonants, retroflex consonants. Further, the method may comprise generating reports based on different properties and cardiovascular health, associated properties and dimensions of organs of the user in order to detect the physiological condition of the organs of the use, wherein the report generated may further be transmitted to the user device.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

Figure 1:
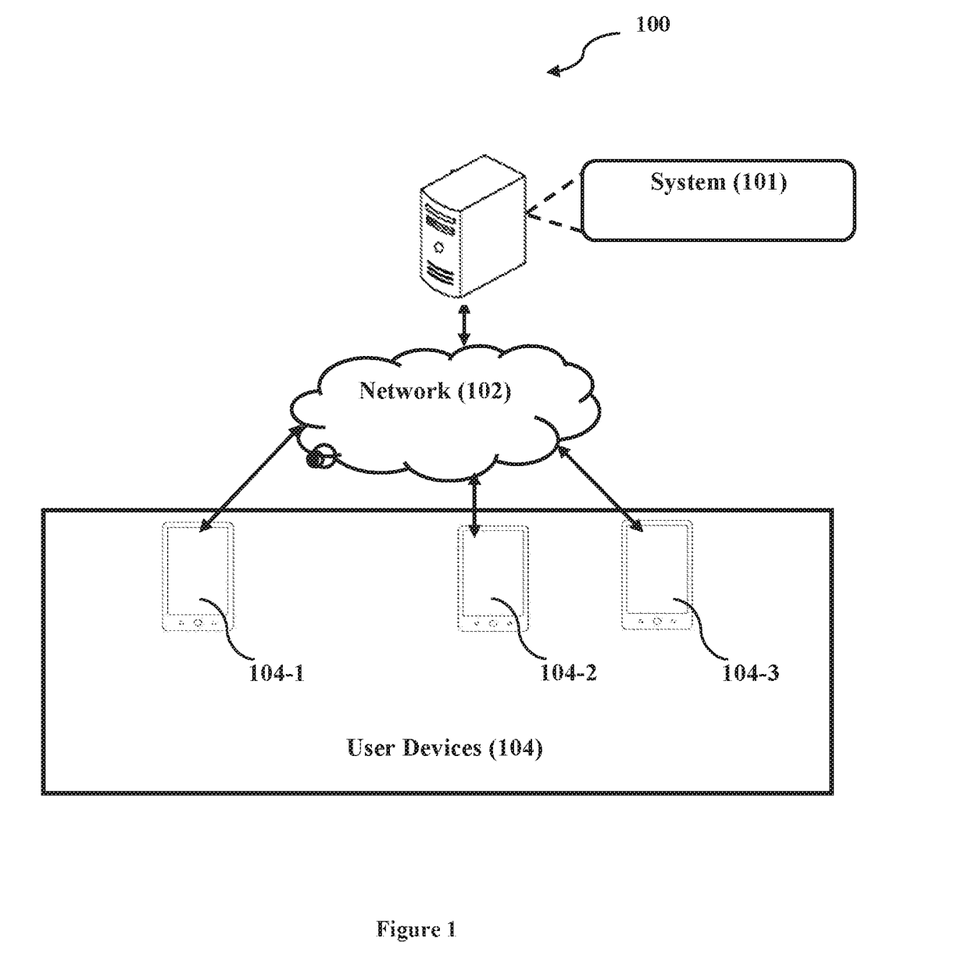
FIG. 1 illustrates, a network implementation 100 of a system 101 for cardiovascular health, associated properties and dimensions of organs of the user by analysing speech samples of the said user, in accordance with an embodiment of a present subject matter.

FIG. 1 illustrates a network implementation 100 of a system 101 for determining cardiovascular health, associated properties and dimensions of user's organ(s) by analysing speech samples of the said user, in accordance with an embodiment of a present subject matter.

In an embodiment, the system 101 may be connected to a user device 104 over a network 102. It may be understood that the system 101 may be accessed by multiple users through one or more user devices 104-1, 104-2, 104-3 . . . 104-n, collectively referred to as user device 104 hereinafter, or applications residing on the user device 104. In an embodiment, as illustrated in FIG. 1, the system 101 may accept information provided by multiple users 104-1,104-2,104-3 using the user device 104 to register the respective user with the system 101.

In an embodiment, though the present subject matter is explained considering that the system 101 is implemented as a server, it may be understood that the system 101 may also be implemented in a variety of user devices, such as a but are not limited to, a portable computer, a personal digital assistant, a handheld device, a mobile, a laptop computer, a desktop computer, a notebook, a workstation, a mainframe computer, and the like. In some embodiments, the system 101 may be implemented in a cloud-based computing environment, a distributing computing environment, and the like. In an embodiment, the network 102 may be a wireless network, a wired network or a combination thereof. The network 102 can be accessed by the device using wired or wireless network connectivity means including updated communications technology.

Figure 2:
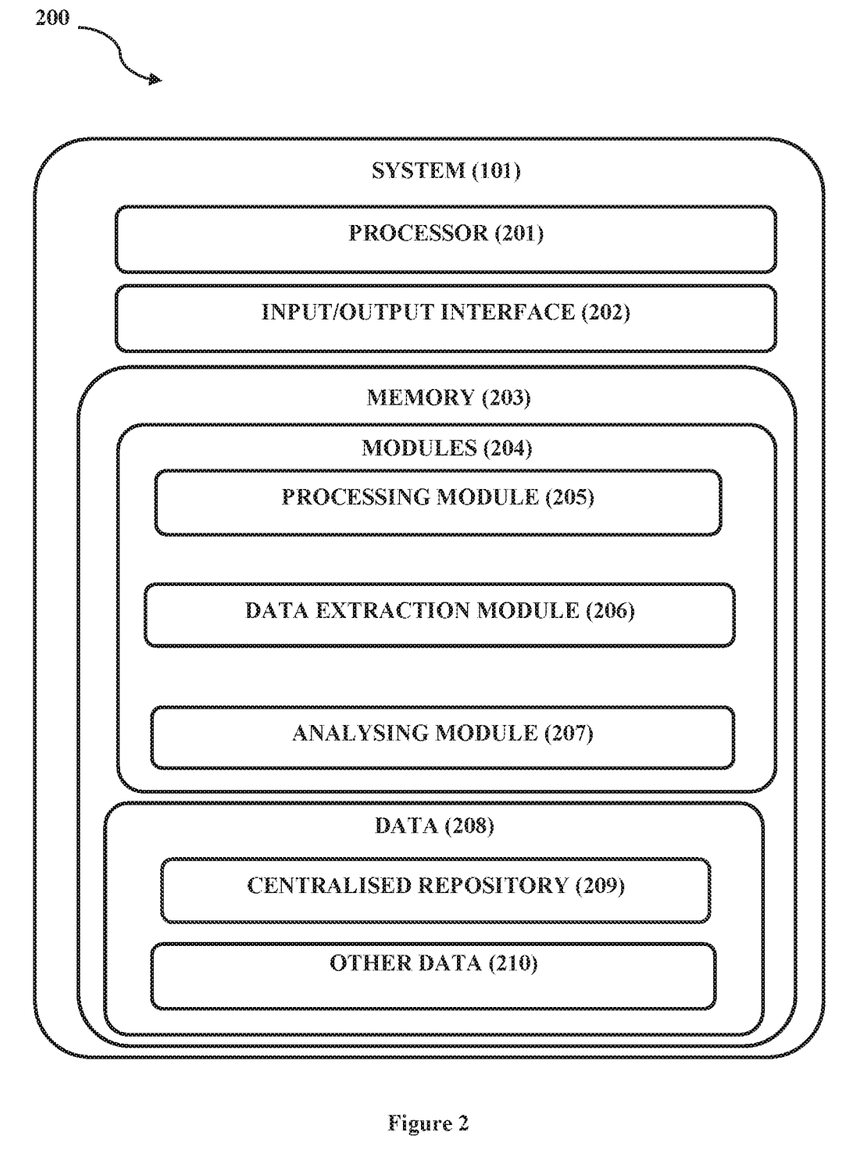
FIG. 2 illustrates, a system 101 and its components, in accordance with an embodiment of a present subject matter.

Now referring to FIG. 2, components of the system 101 are shown which may include at least one processor 201, an input/output (I/O) interface 202, a memory 203, modules 204 and data 208. In one embodiment, the at least one processor 201 is configured to fetch and execute computer-readable instructions stored in the memory 203.

In one embodiment, the I/O interface 202 may include a variety of software and hardware interfaces, for example, a web interface, a Graphical User Interface (GUI), and the like. The I/O interface 202 may allow the system to interact with the user device 104. Further, the I/O interface 202 may enable the system to communicate with other computing devices. The I/O interface 202 can facilitate multiple communications within a wide variety of networks and protocol types, including wired networks, for example, LAN, cable, etc., and wireless networks, such as WLAN, cellular, or satellite.

In one embodiment, the I/O interface 202 is an interaction platform that facilitates interaction between the user device 104 and the system 101. The I/O interface 202 may allow commands for a command line interface or the GUI which may enable a user to create, modify and delete either of data, metadata, program, logic, algorithm, parameters associated with encryption method, encryption program and encryption language.

In one embodiment, the memory 203 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and memory cards. The memory 203 may include modules 204 and data 208.

In one embodiment, the modules 204 may include routines, programs, objects, components, data structure, etc., which performs particular tasks, functions or implement abstract data types. The modules 204 may further include a processing module 205, a data extraction module 206 and an analysing module 207. The data 208 may include a centralized repository 209 and other data 210.

In one embodiment, the user device 104 may guide a user to utter specifics of speech. The user device 104 may record these specifics of speech using a sound recorder (not shown) and may use these specifics of speech as a speech sample of user's utterance. The speech samples may be stored in a local storage of the user device 104. The user device 104 may further record one or more metadata of the user. The user device may transmit the speech samples and the metadata to a system 101 for further processing and analysis.

In one embodiment, the speech samples and the metadata may be stored within the centralized repository 209. In one embodiment, the specifics of speech may include, but not limited to, specific words, letters, phonation, etc. The metadata of the user may include, but are not limited to, user's name, age, location, etc.

In one embodiment, the processing module 205 may process the speech samples by isolating the one or more phonation segments from the speech samples. The processing module 205, may isolate phonation samples for isolating phonation sound using existing phonation isolation techniques/algorithms known in the art. The processing module 205 may further filter the one or more phonation segments in order to remove noise from the one or more phonation segments. The processing module 205 may further isolate the uttered speech segments from the one or more phonation segments using existing phonation segment filtration techniques/algorithms known in the art. The processing module 205 may further isolate the uttered speech segments from the one or more phonation segments.

In one embodiment, the data extraction module 206 may extract the speech features from the uttered speech segments using existing speech feature extraction techniques/algorithms known in the art. The speech features may include, but are not limited to, utterance of the user, vowel and consonants under isolated and/or Vowel Consonant (VC), Consonant Vowel (CV) environment, formants of the utterance, pitch of the utterance, vocal intensity of the utterance, speech quality of the utterance, Vowel Onset Point (VOP), energy transition, values of dispersion and bandwidth, Voice Onset Time (VOT), articulatory rate, shimmer, jitter, spectrogram, etc. The speech features may form a unique set of properties that belong to the user. The unique set of properties that corresponds to the user's current cardiovascular health, associated properties and dimensions of organs of the user may be referred herein as speech markers.

In one embodiment, the speech may have two types of attributes including, frequency and formants. The user's vocal tract is a tube or concatenation of tubes of varying cross-sectional area that is excited either at one end or at a point along the tube. The transfer function of energy from the excitation source to the output can be described in terms of the natural frequency or resonances of the tube. Such resonances are called formants for speech. The formants for speech may represent the frequencies that pass the most acoustic energy from the source of the output. Fant Gunnar, in a publication "Acoustic Theory of Speech Production" Mouton & Co, The Hague, Netherlands, 1960 (hereinafter "Reference 1") defines formants as the spectral peaks of a sound spectrum |P(f)| of the voice. Further, Fant Gunnar., in publication "Acoustic Theory of Speech Production" (1990) (hereinafter "Reference 2") and the Rabiner, L. et. al., in another publication "Digital Processing of Speech Signals", Prentice-Hall, (1978) (hereinafter "Reference 3") collectively proposes that in speech science and phonetics, formant is also used to mean an acoustic resonance of the human vocal tract. Further, according to the Reference 3, the formant is often measured as an amplitude peak in the frequency spectrum of the sound, using a spectrogram. Furthermore, Meurer, Elisea et. al., in a publication "Menstrual Cycle Influences on Voice and Speech in Adolescent Females" (hereinafter "Reference 4") describes that the human vocal tract exhibits four or more major resonances, collectively known as "formants".

Further, in the Reference 1, it has been described that users/speakers carry the anatomical makeup for speech movement and motor capability to achieve the complex movement as per the speech pattern. Furthermore, according to the Reference 1, a general rule in acoustic-articulatory relationship is that F1 frequency varies inversely with tongue height and F2 frequency or the difference between F2 and F1, varies inversely with tongue advancement. F2 variation is known to correspond to the front/back position of the tongue in articulatory terms.

Dr. Will Styler et. al., in a publication "Using Praat for Linguistic Research" document version 1.7 defines VOT as a time between when the stop is released and when the voicing of the following vowel begins. Measuring this time, which can be positive (say, for the English voiceless aspirated stop ta), around zero (for the English "voiced" stop /d/, or, more commonly, the voiceless unaspirated [ta] around the world), or negative (for fully voiced stops, where voicing starts before the stop is released, as found in most non-English languages). Many languages classify their stops largely based on VOT, and it's often an excellent, more gradient empirical measure of the "voiced/voiceless" phonological distinction.

In one embodiment, VOP is the point in time at which the start of the vowel component of the utterance takes place in the speech signal.

In one embodiment, the analysing module 207 may perform an acoustic-phonetic analysis using the extracted speech features of the uttered speech segments in order to determine speech markers and the corresponding cardiovascular health, associated properties and dimensions of organs of the user. The analysing module 207 may use IPA phonemes in order to derive the speech markers that corresponds cardiovascular health, associated properties and dimensions of organs of the user. The IPA phonemes may include, but are not limited to, velar consonants, palatal consonants, retroflex consonants.

In one embodiment, a certain set of speech markers associated with specific cardiological condition can be used to determine the physiological state and cardiovascular health parameters of a user (such as the exact level of an artery blockage in the individual), with a complex mathematical calculation. Thus, after selecting the Speech Markers associated with the cardiological condition and applying the mathematical relationship between those Speech Markers and the cardiological condition, the current condition and specific parameter levels of the cardiovascular health, associated properties and dimensions of organs of the user may be determined.

In one embodiment, the report may be generated based on the cardiological condition, the current condition and specific parameter levels of the cardiovascular health with associated properties the dimensions of different organs. The report may be further transmitted to the user of the user device 104 via the network 102.

Figure 3:
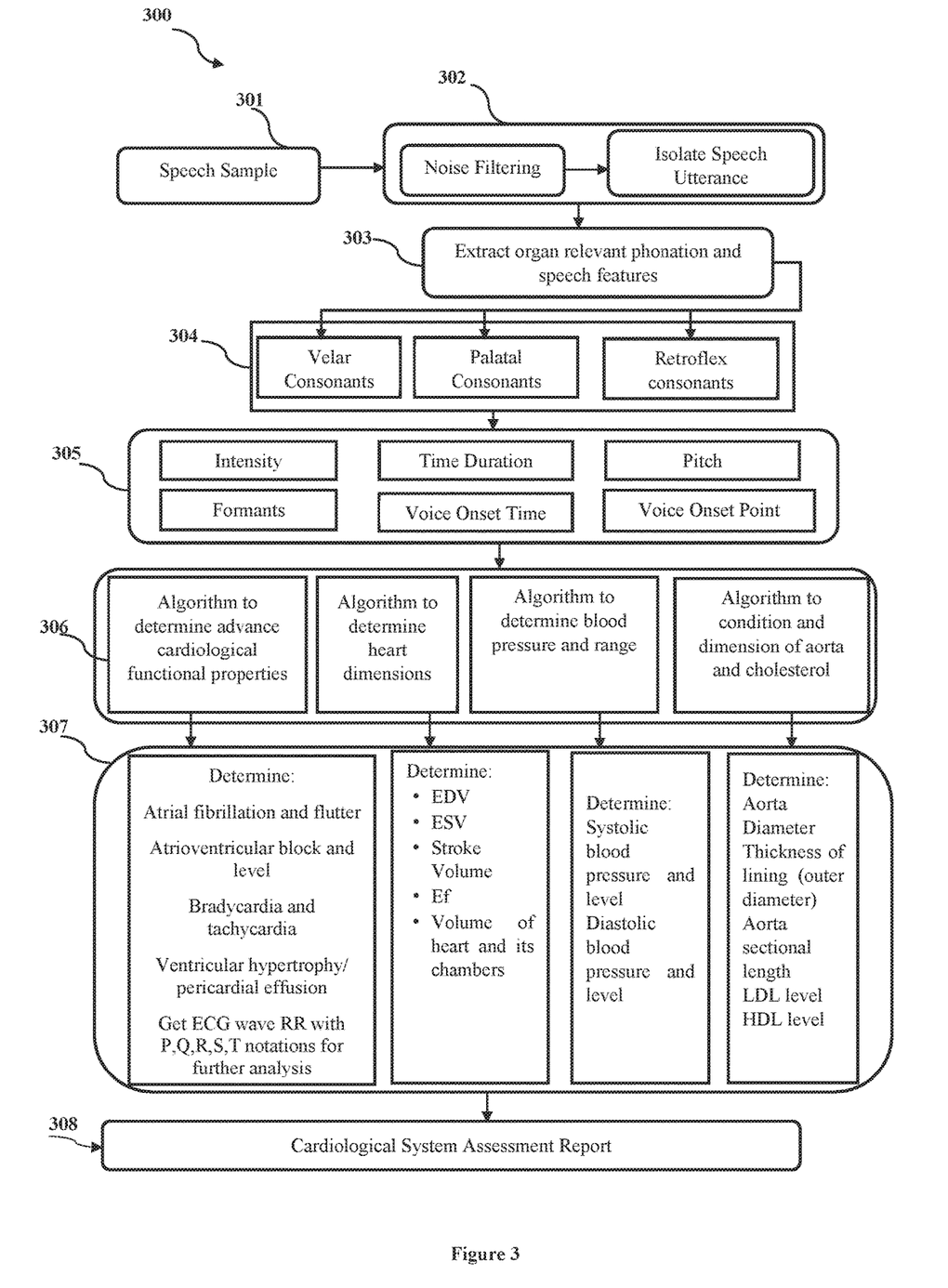
FIG. 3 illustrates, a flow diagram depicting a method for cardiovascular health, associated properties and dimensions of organs of the user, in accordance with an embodiment of a present subject matter.

FIG. 3 illustrates a flow diagram depicting a method for determining cardiovascular health, associated properties and dimensions of user's organ(s) by analysing speech samples of the said user, in accordance with an embodiment of a present subject matter.

At block 301, the user device 104 may record the speech samples by guiding a user to utter specifics of speech. The speech samples may be stored in the local storage of the user device 104. The user device 104 may further record one or more metadata of the user. The user device may transmit the speech samples and the metadata to a system 101 for further processing and analysis.

At block 302, the speech samples may be processed by the processing module 205. The processing module 205 may process the speech samples by isolating the one or more phonation segments from the speech samples. The processing module 205 may further filter the one or more phonation segments in order to remove noise from the one or more phonation segments. The processing module 205 may further isolate the uttered speech segments from the one or more phonation segments.

At block 303, the organ relevant phonation and speech features may be extracted from the uttered speech segments by the data extraction module 206.

At blocks 304, the analysing module 207 may perform the acoustic-phonetic analysis using the extracted speech features of the uttered speech segments in order to determine speech markers and the corresponding cardiovascular health, associated properties and dimensions of organs of the user. In one embodiment, the analysing module 207 may use IPA phonemes in order to derive the speech markers that corresponds to cardiovascular health, associated properties and dimensions of organs of the user.

At block 305, the analysing module 207 may further use the speech features for determining speech markers and the corresponding cardiovascular health, associated properties and dimensions of organs of the user.

At block 306, the analysing module 207 may execute different algorithms which may comprise mathematical formula and/or artificial intelligence to determine cardiovascular health, associated properties and dimensions of user's organ(s).

At block 307, following cardiovascular health parameters are determined
Atrial fibrillation and flutter
Atrioventricular block and level
Bradycardia and tachycardia
Ventricular hypertrophy/pericardial effusion
Get ECG wave RR with P, Q, R, S, T notations for further analysis
Pulse rate (heart rate)
EDV
ESV
Stroke Volume
Ef
Volume of heart and its chambers
Systolic blood pressure and level
Diastolic blood pressure and level
Aorta Diameter
Thickness of lining (outer diameter)
Aorta sectional length
LDL level
HDL level At block 308, the report may be generated based on the cardiovascular health, associated properties and dimensions of user's organ(s). The report may be further transmitted to the user of the user device 104 via the network 102.

In one preferred embodiment, the ECG wave and related parameters are derived from the sound of velar, palatal, and retroflex consonants. The Speech Marker for RR interval consists of summation of the velar, palatal, retroflex consonants time difference of the maximum and minimum value of ratio of formant. As known in the art, RR interval indicates distance between R waves.

In one embodiment, heart rate speech marker is derived by converting RR duration (calculated above) to beats per minute.

In one embodiment, P-wave duration speech marker consists of time difference of the maximum, and minimum value ratio of formants transition points of a voiced unaspirated palatal consonant. As known in the art, the P-wave represents depolarization of the atria. Atrial depolarization spreads from the SA node towards the AV node, and from the right atrium to the left atrium.

In one embodiment, PR-interval speech marker consists of sum of time difference of the maximum and minimum value ratio of formants and associated transition points of a voiced aspirated palatal consonant and nasal palatal consonant. As known in the art, the PR interval is measured from the beginning of the P wave to the beginning of the QRS complex. This interval reflects the time the electrical impulse takes to travel from the sinus node through the AV node.

In one embodiment, PR-segment speech marker consists of time difference of the ratio of the maximum and minimum value of formants transition points of a nasal palatal consonant.

In one embodiment, QRS-duration speech marker consists of the sum of time difference of the maximum value of ratio of formants, and minimum value ratio formant transition points of velar stop consonants. As known in the art, the QRS complex represents the rapid depolarization of the right and left ventricles. The ventricles have a large muscle mass compared to the atria, so the QRS complex usually has a much larger amplitude than the P-wave.

In one embodiment, ST-segment speech marker consists of time difference of the maximum value of ratio of formants, and minimum value ratio of formants transition points of a nasal velar consonant. As known in the art, the ST segment connects the QRS complex and the T wave; it represents the period when the ventricles are depolarized.

In one embodiment, ST-interval speech marker consists of sum of time difference of the maximum value of ratio of formants, and minimum value ratio of formants transition points of a un voiced retroflex consonants and nasal velar consonant.

In one embodiment, T-duration speech marker consists of sum of time difference of the maximum value of ratio of formants, and minimum value ratio of formant transition points of a un voiced palatal consonants. As known in the art, the T wave represents the repolarization of the ventricles. It is generally upright in all leads except aVR and lead V1.

In one embodiment, QT interval speech marker consists of the sum of QRS duration and ST interval. As known in the art, the QT interval is measured from the beginning of the QRS complex to the end of the T wave.

In one embodiment, QTc interval speech marker consists of the ratio of the QT interval to square root of RR duration that were derived in examples above. As known in the art, the QT interval is measured from the beginning of the QRS complex to the end of the T wave. Acceptable ranges vary with heart rate, so it must be corrected to the QTc by dividing by the square root of the RR interval.

In one embodiment, volume and dimensions of heart (length, width, ventricular thickness) may be determined by the fundamental frequency and first formant values of velar consonants, Organ-specific algorithm may be applied which may include a value which is computed statistically, or derived by artificial intelligence, of the speech characteristic to determine dimensions such as length, width, thickness and volume.

In one embodiment, difference of myocardial thickness between left and right myocardial thickness may be determined by the formant length of the unvoiced unaspirated and the voiced aspirated velar consonant, Thickness specific algorithm may be applied which may include a value which is computed statistically, or derived by artificial intelligence, of the speech characteristic to determine dimensions thickness.

In one embodiment, End Systolic Volume (ESV) may be derived from F0 and F1, their corresponding length, sum and average values of unvoiced retroflex and palatal consonants, ESV specific algorithm may be applied which may include a value which is computed statistically, or derived by artificial intelligence, of the speech characteristic, ESV of the right ventricle may be determined by adding the difference of Average, and maximum values of fundamental frequency of unvoiced aspirated retroflex consonant.

In one embodiment, End Diastolic Volume (EDV) may be derived from F0 and F1, their corresponding length, sum and average values of velar consonants, EDV specific algorithm may be applied which may include a value which is computed statistically, or derived by artificial intelligence, of the speech characteristic, EDV of the right ventricle may be determined by adding the difference of Average, and maximum values of fundamental frequency of unvoiced aspirated velar consonant.

In one embodiment, Stroke Volume (SV) may be derived from the difference of ESV and EDV values of unvoiced retroflex and palatal and velar consonants, SV specific algorithm may be applied which may include a value which is computed statistically, or derived by artificial intelligence, of the speech characteristic.

In one embodiment, Ejection Fraction (Et) may be derived from the ratio of SV to EDV values of unvoiced retroflex and palatal and velar consonants, Ef specific algorithm may be applied which may include a value which is computed statistically, or derived by artificial intelligence, of the speech characteristic.

In one embodiment, heart rate speech marker consists of the conversion of the value determined by the ratio of the difference of the difference of the max values of fourth and second formant and min values of fourth and second formant to minute scale of unvoiced unaspirated retroflex consonant, specific algorithm may be applied which may include a value which is computed statistically, or derived by artificial intelligence, of the speech characteristic.

In another embodiment, heart rate speech marker consists of the sum of the ratio of fundamental frequency and value of formants of unvoiced aspirated velar consonant, specific algorithm may be applied which may include a value which is computed statistically, or derived by artificial intelligence, of the speech characteristic.

In one embodiment, speech marker algorithm for pulse pressure consists of the difference of the maximum and the minimum intensity of unvoiced unaspirated retroflex consonant specific algorithm may be applied which may include a value which is computed statistically, or derived by artificial intelligence, of the speech characteristic.

In one embodiment, speech marker algorithm for diastolic blood pressure consists of ratio of the maximum and minimum value of formants to the ratio of minimum and maximum value of intensity of unvoiced unaspirated retroflex consonant, specific algorithm may be applied which may include a value which is computed, statistically, or derived by artificial intelligence, of the speech characteristic.

In one embodiment, speech marker for systolic blood pressure consists the sum of diastolic blood pressure and pulse pressure of unvoiced unaspirated retroflex consonant, specific algorithm may be applied which may include a value which is computed, statistically, or derived by artificial intelligence, of the speech characteristic.

In one embodiment speech markers for the dimensions of aorta i.e. Aortic diameter (Lumen)—(sections-Aortic Annulus, Sinuses of valsalva, Sinotubular junction, Tubular ascending, aorta arch ascending, aorta arch descending, descending tube), Thickness of lining (outer diameter), and Aorta sectional Length consists of the minimum and maximum values of fundamental frequency, intensity of one or more velar, palatal and retroflex consonants, specific algorithm may be applied which may include a value which is computed statistically, or derived by artificial intelligence, of the speech characteristic.

In one embodiment, speech marker algorithm for low-density lipoprotein (LDL) and high-density lipoprotein (HDL), together referred as cholesterol consists of minimum, average and maximum formant values of voiced velar consonant and unvoiced palatal consonants, specific algorithm may be applied which may include a value which is computed, statistically, or derived by artificial intelligence, of the speech characteristic.

EXEMPLARY EMBODIMENTS OF THE PRESENT DISCLOSURE

Exemplary Embodiment 1 (Determining RR Duration)

In this exemplary embodiment, one or more, or a combination of velar, retroflex, and palatal phonation(s) may be used to calculate the RR Duration. Phonation is separated using software known in the prior art. Then the noise from phonation may be filtered out and speech features are extracted. From the extracted features, from the duration of phonation utterance up to VOP point, we calculated RR as below.

TABLE 1

| Phonation(s) | Utterance Duration (Ut) in seconds | RR = UtRetroflex (2/5) + UtPalatal + UtVelar |
|---|---|---|
| Retroflex | 0.32 Sec | RR Duration = 0.32 * 2/5 + |
| Palatal | 0.395 Sec | 0.395 + 0.445 = 0.97 Sec |
| Velar | 0.445 Sec | |

Exemplary Embodiment 2 (Determining Heart Rate)

In this exemplary embodiment, one or more, or a combination of velar, retroflex, and palatal phonation(s) are used to calculate the Heart Rate (HR). Phonation is separated using software known in the prior art. Further the noise from phonation may be filtered out and speech features are extracted. From the extracted features, from the duration of phonation utterance up to VOP point, we calculated HR as below.

TABLE 2

| Phonation(s) | Utterance Duration (Ut) | HR = 60/(UtRetroflex (2/5) + UtPalatal + UtVelar) |
|---|---|---|
| Retroflex | 0.32 sec | HR = 60/(0.32 * 2/5 + 0.395 + |
| Palatal | 0.395 sec | 0.445) = 61 bpm |
| Velar | 0.445 sec | |

The Cases of Bradycardia and Tachycardia may be determined when HR<60 and HR>100 respectively.

Exemplary Embodiment 3 (Determining P Wave Duration)

In this exemplary embodiment, one or more, or a combination of velar, retroflex, and palatal phonation(s) are used to calculate the P wave duration. Phonation is separated using software known in the prior art. Then the noise from phonation may be filtered out and speech features are extracted. From the extracted features, from the duration of phonation utterance up to VOP point, we calculated P wave as below.

TABLE 3

| Phonation(s) | Utterance Duration (Ut) | P Wave duration = duration of voiced un-aspirated palatal consonant |
|---|---|---|
| duration of Voiced un-aspirated Palatal consonant | 0.082 sec | 0.082 sec (82 milliseconds) | ventricular tachycardia is detected when Ut>120 ms

Exemplary Embodiment 4 (Determining PR Interval Duration)

In this exemplary embodiment, one or more, or a combination of velar, retroflex, and palatal phonation(s) are used to calculate the PR interval duration. Phonation is separated using software known in the prior art. Then the noise from phonation may be filtered out and speech features are extracted. From the extracted features, from the duration of phonation utterance up to VOP point, we calculated PR interval as below.

TABLE 4

| Phonation(s) | Utterance Duration (Ut) | PR Interval |
|---|---|---|
| Voiced aspirated Palatal | 0.106 sec | 0.106 + 0.088 = 0.194 sec (194 milliseconds) |
| Palatal nasal | 0.088 sec | |

First degree of atrio-ventricular block is determined If the value of PR Interval>200 ms Exemplary Embodiment 5 (Determining PR Segment)

In this exemplary embodiment, one or more, or a combination of velar, retroflex, and palatal phonation(s) are used to calculate the PR interval duration. Phonation is separated using software known in the prior art. Then the noise from phonation may be filtered out and speech features are extracted. From the extracted features, from the duration of phonation utterance up to VOP point, we calculated PR segment as below.

TABLE 5

| Phonation(s) | Utterance Duration (Ut) | PR Segment |
|---|---|---|
| Duration of Palatal nasal consonant | 0.088 sec | 0.088 Sec |

Exemplary Embodiment 6 (Determining QRS Duration)

In this exemplary embodiment, one or more, or a combination of velar, retroflex, and palatal phonation(s) are used to calculate the PR interval duration. Phonation is separated using software known in the prior art. Then the noise from phonation may be filtered out and speech features are extracted. From the extracted features, from the duration of phonation utterance up to VOP point, we calculated QRS duration as below.

TABLE 6

| Phonation(s) | Utterance Duration (Ut) | QRS Duration = Ut/4 |
|---|---|---|
| Average Duration of Velar consonants (except nasal velar) | 0.32 sec | 0.08 Sec |

Exemplary Embodiment 7 (Determining ST Interval)

In this exemplary embodiment, one or more, or a combination of velar, retroflex, and palatal phonation(s) are used to calculate the ST segment duration. Phonation is separated using software known in the prior art. Then the noise from phonation may be filtered out and speech features are extracted. From the extracted features, from the duration of phonation utterance up to VOP point, we calculated ST interval as below.

TABLE 7

| Phonation(s) | Utterance Duration (Ut) | ST interval = sum(Ut)/2 |
|---|---|---|
| Duration of Velar Nasal consonant | 0.075 sec | (0.075 + 0.056 + 0.075)/2 = 0.103 Sec |
| Duration of two retroflex consonants | 0.056 sec 0.075 sec | |

Exemplary Embodiment 8 (Determining ST Segment)

In this exemplary embodiment, one or more, or a combination of velar, retroflex, and palatal phonation(s) are used to calculate the ST segment duration. Phonation is separated using software known in the prior art. Then the noise from phonation may be filtered out and speech features are extracted. From the extracted features, from the duration of phonation utterance up to VOP point, we calculated ST Segment as below.

TABLE 8

| Phonation(s) | Utterance Duration (Ut) | ST Segment = sum(Ut) |
|---|---|---|
| Duration of Velar Nasal consonant | 0.075 sec | 0.075 Sec |

Exemplary Embodiment 9 (Determining T Wave Duration)

In this exemplary embodiment, one or more, or a combination of velar, retroflex, and palatal phonation(s) are used to calculate the ST segment duration. Phonation is separated using software known in the prior art. Then the noise from phonation may be filtered out and speech features are extracted. From the extracted features, from the duration of phonation utterance up to VOP point, we calculated ST Segment as below.

TABLE 9

| Phonation(s) | Utterance Duration (Ut) | T wave duration = sum(Ut) |
|---|---|---|
| Lower value of sum of duration of voiced unaspirated Palatal | 0.075 sec | 0.169 Sec |
| duration of Voiced aspirated Palatal consonant | 0.094 sec | |

Exemplary Embodiment 10 (Determining QT Interval)

In this exemplary embodiment, one or more, or a combination of velar, retroflex, and palatal phonation(s) are used to calculate the ST segment duration. Phonation is separated using software known in the prior art. Then the noise from phonation may be filtered out and speech features are extracted. From the extracted features, from the duration of phonation utterance up to VOP point, we calculated QT interval as below.

TABLE 10

| Phonation(s) | Utterance Duration (Ut) | | QT Interval |
|---|---|---|---|
| QRS Duration - Duration of Velar consonants (except nasal velar) | 0.32 sec | QRS duration = Ut/4 = 0.08 Sec | (0.08 + 0.075 + 0.056 + 0.075)* 1.25 = 0.3575 sec |
| Duration of Velar Nasal consonant | 0.075 sec | (0.075 + 0.056 + 0.075) = 0.206 Sec | |
| Duration of two retroflex consonants | 0.056 sec 0.075 sec | | |

Exemplary Embodiment 11 (Determining QT c Interval)

In this exemplary embodiment, one or more, or a combination of velar, retroflex, and palatal phonation(s) are used to calculate the QT c Interval duration. Phonation is separated using software known in the prior art. Then the noise from phonation may be filtered out and speech features are extracted. From the extracted features, from the duration of phonation utterance up to VOP point, we calculated QT c Interval as below.

TABLE 11

| QTc Interval | =QT interval/square root of R – R duration = 0.3575 (from example 10 above)/√0.971 = 0.3625 sec |
|---|---|

Exemplary Embodiment 12 (Determining Volume and Dimension of Heart)

In this exemplary embodiment, one or more, or a combination of velar, retroflex, and palatal phonation(s) are used to calculate the volume and dimension of heart. Phonation is separated using software known in the prior art. Then the noise from phonation may be filtered out and speech features are extracted. From the extracted features, we calculated dimension of heart as below.

TABLE 12

Length (L) = (Average Frequency of 3 velar consonants) * 3/40 = 161.17 *3/40 = 12.08 cm
Width (W) = sum of ((8507/formant)/6) of 3 velar consonants = 53.87/6 = 8.9 cm
Thickness (T) = average of ((8507/formant)/3) of 3 velar consonants = 17.95/3 = 5.98 cm
Volume = L*W*T * 0.87/8 = 69.91 ml

Exemplary Embodiment 13 (Determining Myocardial Thickness)

In this exemplary embodiment, one or more, or a combination of velar, retroflex, and palatal phonation(s) are used to calculate the Myocardial thickness of heart. Phonation is separated using software known in the prior art. Then the noise from phonation may be filtered out and speech features are extracted. From the extracted features, we calculated Myocardial thickness of heart as below.

TABLE 13

Left ventricular thickness = (8507/formant) of voiced
    un-aspirated Velar * 0.65
    = 17.47 * 0.65
    = 11.35 mm
Right ventricular thickness = (8507/formant) of voiced
    aspirated Velar * 0.65
    = 14.92 * 0.65
    = 9.6 mm
Difference of myocardial thickness between Left and Right ventricle = 11.35 - 9.6 = 1.75 mm

Exemplary Embodiment 14 (Determining ESV (End Systole Volume))

In this exemplary embodiment, one or more, or a combination of velar, retroflex, and palatal phonation(s) may be used to calculate the ESV of heart. Phonation is separated using software known in the prior art. Then the noise from phonation may be filtered out and speech features are extracted. From the extracted features, we calculated ESV of heart as below.

TABLE 14

Length (L) = (Average Frequency voiced aspirated retroflex, voiced un-aspirated retroflex, and palatal consonant) * 3/40 = 163.27 *3/40 = 12.28 cm
Width (W) = sum of ((8507/formant)/6) of voiced aspirated retroflex, voiced un-aspirated retroflex, and palatal consonant) = 45.77/6 = 7.62 cm TABLE 14-continued ESV of Left ventricle (ESVLV) = 0.26 * W2 * L * 0.25 = 46.64 ml
ESV of Right ventricle (ESVRV) = ESVLV + (Difference of MAX F0) - (Average of F0 of Unvoiced aspirated Retroflex consonant) = 46.64 + 2.18 = 48.82 ml

Exemplary Embodiment 15 (Determining EDV (End Diastole Volume), Stroke Volume (SV), Ejection Fraction ($E_f$))

In this exemplary embodiment, one or more, or a combination of velar, retroflex, and palatal phonation(s) may be used to calculate the EDV of heart. Phonation is separated using software known in the prior art. Then the noise from phonation may be filtered out and speech features are extracted. From the extracted features, we calculated EDV, SV, Ef of heart as below.

TABLE 15 (a)

Length (L) = (Average Frequency unvoiced aspirated velar, unvoiced un-aspirated velar, and voiced velar consonant) * 3/40 = 168.12 *3/40 = 12.6 cm
Width (W) = sum of ((8507/formant)/6) of unvoiced aspirated velar, unvoiced un-aspirated velar, and voiced velar consonant = 57.29/6 = 9.54 cm
Width (T) = sum of ((8507/formant)/3) of unvoiced aspirated velar, unvoiced un-aspirated velar, and voiced velar consonant = 19.09/6 = 6.33 cm
Net Volume = L * W * T * 3 * 0.25 = 68.58 ml TABLE 15 (b)

EDVLV = ESV + Net Volume
    = 46.64 + 68.58 = 115.22 ml

EDVRV = EDVLV + (Max $F_0$ - Average $F_0$) of voiced
    aspirated Velar consonant
    = 115.22 + 1.68
    = 116.9 ml Stroke Volume (SV) = EDV - ESV
    = (EDVLV - ELVLV) OR (EDVRV - ELVRV)
    = 68.58 OR 68.35
    = ~68 ml Ejection Fraction (Ef) = SV/EDV
    = 68/115
    = 58.84%

Exemplary Embodiment 15 (Determining (Heart Rate))

In this exemplary embodiment, one or more, or a combination of velar, retroflex, and palatal phonation(s) are used to calculate the heart rate. Phonation is separated using software known in the prior art. Then the noise from phonation may be filtered out and speech features are extracted. From the extracted features, from the duration of phonation utterance up to VOP point, we calculated heart rate as below.

TABLE 15

Heart rate = 60 * (F4MAX − F2 MAX)/(F2MIN − F2MIN)

= 60 * 2665/2417

= 66 bpm

Exemplary Embodiment 16 (Determining Pulse Pressure, Diastolic Pressure and Systolic Pressure)

In this exemplary embodiment, one or more, or a combination of velar, retroflex, and palatal phonation(s) are used to calculate the pulse, diastolic and systolic pressure. Phonation is separated using software known in the prior art. Then the noise from phonation may be filtered out and speech features are extracted. From the extracted features, from the duration of phonation utterance up to VOP point, we calculated pulse, diastolic and systolic pressure as below.

TABLE 16

Pulse Pressure = Difference if minimum and maximum intensity of phonation + (sum of min and max Intensity of phonation)/2 = 10 + 61 = 71

Diastolic pressure = (60 * F4 MAX) *

(Intensity Max) / F4MIN * (Intensity MIN)

= (60/0.7) / 0.84

= 88

Systolic Pressure = Diastolic pressure + Pulse Pressure

= 88 + 71 = 159

Exemplary Embodiment 17 (Determining Dimensions of Aorta—[A] Aorta Dimensions [B] Outer Diameter of Aorta [C] Sectional Length)

In this exemplary embodiment, one or more, or a combination of velar, retroflex, and palatal phonation(s) are used to calculate dimensions of Aorta. Phonation is separated using software known in the prior art. Then the noise from phonation may be filtered out and speech features are extracted. From the extracted features, from the duration of phonation utterance up to VOP point, we calculated Aorta dimensions as below.

VUAV=Velar Unaspirated Voiced

VAV=Velar aspirated voiced

RUAU=retroflex unaspirated unvoiced

PUAV=palatal unaspirated voiced

TABLE 17

Aortic Annulus diameter = [(8507/F0MIN of VUAV) − (8507/F0MAX of VUAV)] * (F0MIN of VUAV/F0MAX of VUAV) * (Intensity MIN of VUAV/Intensity MAX of VUAV) * 10 = 3.6 * 0.92 * 0.77 * 10 = 26.24 mm
Sinuses of Valsalva = [(8507/F0MIN of VAV) − (8507/F0MAX of VAV)] * (F0MIN of VAV/F0MAX of VAV) * (Intensity MIN of VAV/Intensity MAX of VAV) * 10 = 5.99 * 0.88 * 0.82 * 10 = 43.77 mm
Sinotubular junction = [(8507/F0MIN of RUAU) − (8507/F0MAX of RUAU)] * (F0MIN of RUAU/F0MAX of RUAU) * (Intensity MIN of RUAU/Intensity MAX of RUAU) * 10 = 4.57 *0.9 * 0.75 * 10 = 31.68 mm

TABLE 17-continued

Tubular ascending = [(8507/F0MIN of PUAV) − (8507/F0MAX of RUAU)] * (F0MIN of RUAU/F0MAX of RUAU) * (Intensity MIN of RUAU/Intensity MAX of RUAU) * 10 = 4.57 * 0.9 * 0.75 * 10 = 31.68 mm
Aorta arch ascending = [(8507/F0MIN of VUAV) − (8507/F0MAX of VUAV)] * (F0MIN of VUAV/F0MAX of VUAV) * (Intensity MIN of VUAV/Intensity MAX of VUAV) * 10/4 = 20.12 * 0.66 * 0.66 * 10/4 = 22.18 mm
Aorta descending = [(8507/F0MIN of VAV) − (8507/F0MAX of VUAV)] * (F0MIN of VAV/ F0MAX of VAV) * (Intensity MIN of VAV/Intensity MAX of VAV) * 10/4 = 13.87 * 0.78 * 0.84 * 10/4 = 22.90 mm
Aorta ascending = [(8507/F0MIN of PUAV) − (8507/F0MAX of PUAV)] * (F0MIN of PUAV/F0MAX of PUAV) * (Intensity MIN of PUAV/Intensity MAX of PUAV) * 10/2 = 7.3 * 0.86 * 0.68 * 10/2 = 22.18 mm
Outer diameter of Aorta (Lining thickness) = Average Length of Palatal aspirated voiced - Average Length of Velar unaspirated voiced = 48.48 − 38.18 = 2.2 mm
Net thickness = Lining thickness/200 = 2.2/200 = 0.011 mm
Section Length AB = (Time duration of Palatal, Velar, Retroflex consonants)/4 * 1000 = 0.07675 * 1000 = 76.75 mm Section Length BC = Time duration of Velar aspirated and unaspirated/4 * 1000

= 0.03775 * 1000 = 37.75 mm

Section Length CD = $\dfrac{\text{Time duration of Palatal}}{\text{unaspirated voiced}}/4 * 1000$ = 0.94 * 1000 = 94.0 mm

Exemplary Embodiment 18 (Determining Cholesterol Estimation (Total, LDL, HDL, Triglycerides)

In this exemplary embodiment, one or more, or a combination of velar, retroflex, and palatal phonation(s) are used to calculate cholesterol. Phonation is separated using software known in the prior art. Then the noise from phonation may be filtered out and speech features are extracted. From the extracted features, from the duration of phonation utterance up to VOP point, we calculated cholesterol as below.

TABLE 18 (a)

D = (F3AVG/F1 AVG) + (F3 AVG/F2 AVG) + (F2 AVG/F1 AVG) + (F4 AVG/F3 AVG); K = (D + 0.02 D); Kr = K* F2/F3; KrAVG = for average values; KrMAX = for max values D is a variable that represents the spectral slope, differentiating involved speech signals. To account for normal variation of 20%, calculations have been adjusted in formula K=(D+0.02 D)

The speech parameters are specific to the person (sample) and a rationalization is needed to make a generalized approach. The dynamic factor is defined in variable Kr.

TABLE 18 (b)

| Phonation | KrAVG (a) | KrMAX (b) |
|---|---|---|
| Velar un-aspirated voiced | 5.65 | 3.89 |
| Velar aspirated voiced | 4.49 | 5.16 |
| Palatal un-aspirated voiced | 4.99 | 4.78 |
| Palatal aspirated voiced | 4.74 | 3.94 |
| Column average | 4.96 | 4.44 |

TABLE 18 (c)

Total cholesterol = (Average of column (a)/2) *100 = (4.96/2) *100 = 248
HDL = minimum value in column (b) * 10 = 3.89 *10 = 38.9
Ratio of total to HDL = 248/38.9 = 6.37
LDL = Total cholesterol/[(ratio of total to HDL) + maximum value of column (a) + maximum value of column (b)] * 10 = (248/[6.37 + 5.56 + 5.16]) *10 = 144.3
Triglycerides = Total cholesterol − (HDL + LDL) = 248 − (38.9 + 144.3) = 64.8

Although implementations for a system and method for determining cardiovascular health associated properties and physiological properties by analysing speech samples of said user have been described in language specific to structural features and/or methods, it is to be understood that the appended claims are not necessarily limited to the specific features or methods described. Rather, the specific features and methods are disclosed as examples of implementations for determining cardiovascular health associated properties and dimensions of a of user's organ(s) by analysing speech samples of user.

The invention claimed is:

1. A system (101) for determining cardiovascular health, associated properties, and dimensions of user's cardiovascular organs by analysing speech samples, the system comprising:
a processor (201); and
a memory (203) coupled with the processor, wherein the processor is configured to execute a plurality of programmed instructions stored in the memory (203), the plurality of programmed instructions comprising instructions for:
interactively guiding a user to utter specifics of a speech via a user device (104) communicatively coupled with the processor (201);
recording, via the user device, one or more speech samples associated with the user based upon the specifics of speech uttered by the user;
isolating one or more phonation segments from the one or more speech samples;
filtering one or more phonation segments to remove noise from the one or more phonation segments;
isolating one or more uttered speech segments from the one or more phonation segments filtered;
performing acoustic-phonetic analysis of the one or more uttered speech segments to extract one or more speech features; and
determining one or more speech markers and the corresponding cardiovascular health parameters, associated properties, and dimensions of one or more cardiovascular organs of the user based upon the one or more speech features.

2. The system according to claim 1, wherein the specifics of speech comprises attributes selected from a group comprising of one or more frequencies, one or more formants, one or more intensities, or combinations thereof, and wherein the specifics of speech comprises one or more of words, letters, and phonations.

3. The system according to claim 1, wherein the one or more speech features comprises utterance of the user, vowel, consonant vowel consonant (VC), consonant Vowel (CV), formants of the utterance, pitch of the utterance, vocal intensity of the utterance, speech quality of the utterance, vowel onset point (VOP), energy transition, values of dispersion and bandwidth, voice onset time (VOT), articulatory rate, shimmer, jitter, and spectrogram.

4. The system according to claim 1, wherein the speech markers corresponding to the cardiovascular health parameters comprises cardiovascular health markers, associated properties, and dimensions of one or more cardiovascular organs of the user, wherein the cardiovascular health parameters comprise ECG wave heart rate speech marker, P-wave duration speech marker, PR-interval speech marker, PR-segment speech marker, QRS-duration speech marker, ST-segment speech marker, ST-interval speech marker, T-duration speech marker, QT interval speech marker, QTc interval speech marker, volume and dimensions of heart, difference of myocardial thickness between left and right myocardial thickness, End Systolic Volume (ESV) speech marker, End Diastolic Volume (EDV), Stroke Volume (SV) speech marker, Ejection Fraction (Ef) speech marker, heart rate speech marker, pulse pressure speech marker, diastolic blood pressure speech marker, systolic blood pressure speech marker, dimensions of aorta speech marker, and cholesterol speech marker, wherein the speech markers corresponding to the cardiovascular health parameters are determined using International Phonetic alphabets (IPA) phonemes selected from one or more velar consonants, one or more palatal consonants, one or more retroflex consonants or combinations thereof.

5. The system according to claim 4, wherein the cardiovascular health parameters corresponding to a distance between R waves determined from RR interval speech marker is summation of the velar, palatal, retroflex consonants time difference of a maximum and minimum value of ratio of formant, and wherein the cardiovascular health parameters corresponding to the heart rate speech marker is determined by converting RR duration to beats per minute.

6. The system according to claim 4, wherein the cardiovascular health parameters corresponding to the P-wave duration speech marker is an index of a speech marker, and wherein cardiovascular health parameters corresponding to the PR-interval speech marker is a sum of time difference of maximum and minimum value ratio of formants, associated transition points of a voiced aspirated palatal consonant and nasal palatal consonant, and wherein the cardiovascular health parameters corresponding to the PR-segment speech marker is a time difference of ratio of maximum and minimum value of formants transition points of a nasal palatal consonant.

7. The system according to claim 4, wherein the cardiovascular health parameters corresponding to the QRS-duration speech marker is a sum of time difference of maximum value of ratio of formants and minimum value ratio formant transition points of velar stop consonants, and wherein the cardiovascular health parameters corresponding to the ST-segment speech marker is a time difference of the maximum value of ratio of formants and minimum value ratio of formants transition points of a nasal velar consonant, and wherein the cardiovascular health parameters corresponding to the T-duration speech marker is a sum of time difference of the maximum value of ratio of formants and minimum value ratio of formant transition points of an unvoiced palatal consonants.

8. The system according to claim 4, wherein the cardiovascular health parameters corresponding to the QT interval speech marker is a sum of QRS duration and ST interval, and wherein the cardiovascular health parameters corresponding to the QTc interval speech marker is a ratio of the QT interval to square root of RR duration.

9. The system according to claim 4, wherein the cardiovascular health parameters corresponding to the volume and dimensions of heart is determined by a fundamental frequency and first formant values of velar consonants.

10. The system according to claim 4, wherein the cardiovascular health parameters corresponding to the difference of myocardial thickness between left and right myocardial thickness is determined as formant length of unvoiced unaspirated and voiced aspirated velar consonant.

11. The system according to claim 4, wherein the cardiovascular health parameters corresponding to the End Systolic Volume (ESV) speech marker is determined from F0 and F1, and length, sum, and average values of unvoiced retroflex and palatal consonants, and wherein the cardiovascular health parameters corresponding to the End Diastolic Volume (EDV) speech marker is determined from F0 and F1, and length, sum, and average values F0 and F1, and length, sum, and average values of velar consonants, and wherein the cardiovascular health parameters corresponding to the Stroke Volume (SV) speech marker is determined from a difference of ESV and EDV values of unvoiced retroflex, palatal, and velar consonants, and wherein the cardiovascular health parameters corresponding to the Ejection Fraction (Ef) speech marker is determined from a ratio of SV to EDV values of unvoiced retroflex, palatal, and velar consonants.

12. The system according to claim 4, wherein the cardiovascular health parameters corresponding to the heart rate speech marker is determined from a sum of ratio of fundamental frequency and value of formants of unvoiced aspirated velar consonant, and wherein the cardiovascular health parameters corresponding to the pulse pressure speech marker is determined from a difference of maximum and minimum intensity of unvoiced unaspirated retroflex consonant.

13. The system according to claim 4, wherein the cardiovascular health parameters corresponding to the diastolic blood speech marker is determined from a ratio of maximum and minimum value of formants to the ratio of minimum and maximum value of intensity of unvoiced unaspirated retroflex consonant, and wherein the cardiovascular health parameters corresponding to the systolic blood pressure speech marker is determined from a sum of diastolic blood pressure and pulse pressure of unvoiced unaspirated retroflex Consonant.

14. The system according to claim 4, wherein the cardiovascular health parameters corresponding to the dimensions of aorta speech marker is determined at least from minimum and maximum values of fundamental frequency of unvoiced aspirated velar consonant, intensity of one or more velar, palatal, and retroflex consonants.

15. The system according to claim 4, wherein the cardiovascular health parameters corresponding to the cholesterol speech marker is determined from a minimum, average, and maximum formant values of voiced velar consonant and unvoiced palatal consonants.

16. A method for determining cardiovascular health, associated properties, and dimensions of user's cardiovascular organs by analysing speech samples comprising:
  interactively guiding, via a user device communicatively coupled with a processor, a user to utter specifics of a speech;
  recording, via the user device, one or more speech samples associated with the user based upon the specifics of speech uttered by the user;
  isolating, via the processor, one or more phonation segments from the one or more speech samples;
  filtering, via the processor, one or more phonation segments to remove noise from the one or more phonation segments;
  isolating, via the processor, one or more uttered speech segments from the one or more phonation segments filtered;
  performing, via the processor, acoustic-phonetic analysis of the one or more uttered speech segments to extract one or more speech features; and
  determining, via the processor, one or more speech markers and the corresponding cardiovascular health, associated properties, and dimensions of one or more cardiovascular organs of the user based upon the one or more speech features.

17. The method according to claim 16, further comprising generating, via the processor, reports based on cardiovascular health, associated properties, and dimensions of one or more cardiovascular organs of the user in order to determine cardiovascular health, associated properties, and dimensions of user's cardiovascular organs, wherein the report generated may further be transmitted to the user device.

* * * * *